United States Patent
Frautschi et al.

(10) Patent No.: US 9,913,934 B2
(45) Date of Patent: Mar. 13, 2018

(54) RADIOPAQUE, OPTICALLY TRANSLUCENT THERMOPLASTIC COMPOUNDS

(71) Applicant: PolyOne Corporation, Avon Lake, OH (US)

(72) Inventors: Jack Frautschi, Avon Lake, OH (US); Jing Liu, Avon, OH (US); Jiannong Xu, Westlake, OH (US)

(73) Assignee: PolyOne Corporation, Avon Lake, OH (US)

( * ) Notice: Subject to any disclaimer, the term of this patent is extended or adjusted under 35 U.S.C. 154(b) by 62 days.

(21) Appl. No.: 14/916,687

(22) PCT Filed: Sep. 8, 2014

(86) PCT No.: PCT/US2014/054499
§ 371 (c)(1),
(2) Date: Mar. 4, 2016

(87) PCT Pub. No.: WO2015/035282
PCT Pub. Date: Mar. 12, 2015

(65) Prior Publication Data
US 2016/0220735 A1 Aug. 4, 2016

Related U.S. Application Data

(60) Provisional application No. 61/874,942, filed on Sep. 6, 2013, provisional application No. 61/920,536, filed on Dec. 24, 2013.

(51) Int. Cl.

| | |
|---|---|
| *A61L 29/18* | (2006.01) |
| *G21F 1/10* | (2006.01) |
| *C08K 3/30* | (2006.01) |
| *C08L 75/04* | (2006.01) |
| *C09J 175/04* | (2006.01) |
| *A61L 29/02* | (2006.01) |
| *A61L 29/06* | (2006.01) |
| *C08K 5/00* | (2006.01) |
| *C08G 101/00* | (2006.01) |

(52) U.S. Cl.
CPC ............ *A61L 29/18* (2013.01); *A61L 29/02* (2013.01); *A61L 29/06* (2013.01); *C08K 3/30* (2013.01); *C08L 75/04* (2013.01); *C09J 175/04* (2013.01); *G21F 1/10* (2013.01); *A61L 2400/12* (2013.01); *C08G 2101/00* (2013.01); *C08K 5/0008* (2013.01); *C08K 2201/011* (2013.01)

(58) Field of Classification Search
CPC ........................................................ A61L 29/18
See application file for complete search history.

(56) References Cited

U.S. PATENT DOCUMENTS

| | | | |
|---|---|---|---|
| 5,183,614 A | * | 2/1993 | Champion .............. D01F 1/106 |
| | | | 264/184 |
| 6,200,338 B1 | | 3/2001 | Solomon et al. |
| 6,641,776 B1 | | 11/2003 | Weaver et al. |
| 7,182,997 B2 | | 2/2007 | Murschall et al. |
| 7,575,734 B2 | | 8/2009 | Berkei et al. |
| 7,632,765 B2 | | 12/2009 | Shalaby et al. |
| 8,119,716 B2 | * | 2/2012 | Hardinghaus .......... B82Y 30/00 |
| | | | 524/133 |
| 9,034,229 B2 | | 5/2015 | Hsiao et al. |
| 2007/0140938 A1 | | 6/2007 | Stahl et al. |
| 2008/0227901 A1 | | 9/2008 | Lefevre et al. |
| 2009/0318594 A1 | | 12/2009 | Grothe et al. |
| 2009/0326114 A1 | * | 12/2009 | Grothe ..................... C08K 3/30 |
| | | | 524/148 |
| 2010/0300449 A1 | | 12/2010 | Chan et al. |
| 2012/0294919 A1 | * | 11/2012 | Jaynes .................. A01N 25/08 |
| | | | 424/404 |

FOREIGN PATENT DOCUMENTS

| | | |
|---|---|---|
| EP | 0335159 A1 | 10/1989 |
| EP | 0452123 B1 | 1/1996 |
| JP | 9-38194 A | 2/1997 |
| WO | 95/14501 A1 | 6/1995 |
| WO | 2008135545 A1 | 11/2008 |

OTHER PUBLICATIONS

Romero Ibarra et al. "Preparacion de un nanocompuesto polimero-BaSO4 con potencial aplicacion biomedica," (Not Dated).

* cited by examiner

*Primary Examiner* — Michael Pepitone
(74) *Attorney, Agent, or Firm* — Michael J. Sambrook; Maria M. Hoke; John H. Hornickel

(57) ABSTRACT

A radiopaque, optically translucent thermoplastic polyurethane compound is disclosed. The use of nano-sized particles of barium sulfate optionally in combination with a minor amount of certain dispersion aids allows the barium sulfate to be sufficiently dispersed within the thermoplastic polyurethane to retain optical translucency according to a defined Haze Determination Test. Medical devices, needing both visual spectrum observation before and during in-vivo medical use and radiopacity monitoring during in-vivo medical use, benefit from this compound. Optionally, a surface enhancer can also be used.

11 Claims, No Drawings

RADIOPAQUE, OPTICALLY TRANSLUCENT THERMOPLASTIC COMPOUNDS

CLAIM OF PRIORITY

This application claims priority from U.S. Provisional Patent Application Ser. No. 61/874,942 filed on Sep. 6, 2013 and U.S. Provisional Patent Application Ser. No. 61/920,536 filed on Dec. 24, 2013, which are incorporated by reference.

FIELD OF THE INVENTION

This invention relates to thermoplastic compounds which are translucent in the visible spectrum but radiopaque to x-rays and other diagnostic imaging using electromagnetic radiation.

BACKGROUND OF THE INVENTION

The world of polymers has progressed rapidly to transform material science from wood and metals of the $19^{th}$ Century to the use of thermoset polymers of the mid-$20^{th}$ Century to the use of thermoplastic polymers of later $20^{th}$ Century.

Thermoplastic compounds are often used in the healthcare industry as hygienically disposable items. Catheters for in-vivo diagnosis and treatment are often constructed from thermoplastic polyurethanes. Optically translucent thermoplastic polyurethanes are preferred because the health care practitioner can see through the wall of the catheter before and during in-vivo usage. Delivery of fluids containing air bubbles could be avoided (producing air emboli if in the blood), for example, by using an optically translucent, medical grade thermoplastic polyurethane.

During in-vivo usage, many diagnostic or therapeutic medical devices are monitored by the use of x-rays, using an energy of 30-70 keV, and other diagnostic electromagnetic radiation. Radiopaque materials in the medical device offer a contrast during such monitoring, such to recognize the precise location of a catheter tip and shaft as it moves within the body of the patient undergoing a medical procedure. Yet radiopaque materials, as helpful during in-vivo usage as they are, have the detriment of reducing severely the optical translucency of medical device before and during an in-vivo usage.

PCT Patent Publication WO95/14501 teaches that a radiopaque material can be present in thermoplastic material in an amount from 5 to 50 percent by weight in levels to be adjusted to achieve both a radiopaque and translucent material for a balloon catheter. But there is no additional detail to explain how to disperse the proper amounts of polymer and radiopaque material. Moreover, this publication does not teach the use of thermoplastic polyurethane as a candidate for the balloon catheter.

SUMMARY OF THE INVENTION

What the art of medical devices needs is a radiopaque material and other ingredients to be intimately and thoroughly mixed and dispersed within thermoplastic polyurethane, such that the resulting medical device is both optically translucent and radiopaque.

The present invention solves that problem by using nano-sized particles of barium sulfate with an optional dispersing aid and thoroughly dispersing both in the thermoplastic polyurethane, so as to achieve both optical translucency through the wall of the medical device and also radiopacity of the medical device via imaging during in-vivo diagnostic or therapeutic medical procedures.

"Nano-sized particles of barium sulfate" means barium sulfate which has more than 50% of the primary particles of the barium sulfate having a size in the largest dimension of less than or equal to 100 nanometers. "Primary particles" means the smallest particles of barium sulfate, as observed by high resolution scanning electron microscopy (SEM), even though those particles might stick to each other to form aggregates or agglomerates.

The nano-sized particles of barium sulfate radiopaque material can have aggregates or agglomerates of the primary particles (with dimensions in the range of 1-10 μm) without departing from the scope of the present invention. It is preferable for the aggregates and agglomerates to be minimized in number and volume, such as by milling the barium sulfate before use. Also, with the assist from an optional dispersing aid such as propylene glycol, the separation of such primary particles from aggregates or agglomerates, resulting in more than 50% of the particles having a largest dimension less than 100 nm, smaller than the wavelengths of the visible spectrum, permits the thermoplastic polyurethane to retain as much of its original optical translucency as is feasible.

One aspect of the present invention is a radiopaque, optically translucent thermoplastic compound, comprising thermoplastic polyurethane; nano-sized particles of barium sulfate dispersed in the thermoplastic polyurethane at 10 weight percent to 50 weight percent of the compound; and optionally a dispersion aid selected from the group consisting of polyols (diols, triols, etc.), sulfolane, triethyl citrate, 1-methyl-2-pyrrolidinone, and combinations thereof; wherein a compressed film of the compound in a thickness of 0.18 mm has a haze of less than 75%, as measured using a Haze Determination Test if the dispersion aid is not present in the compound; and wherein a compressed film of the compound in a thickness of 0.18 mm has a haze of less than 70%, as measured using a Haze Determination Test if the dispersion aid is present in the compound.

Optionally, one can also include a surface enhancer to reduce roughness of external surfaces of an in-vivo medical device.

Another aspect of the invention is an in-vivo medical device made from the radiopaque, optically translucent thermoplastic compound.

For avoidance of doubt, "optically translucent" means that a person with normal eyesight or using corrective lenses to normal vision can see through a sample of the thermoplastic compound in a film of a thickness of between 5 and 10 mils (0.127-0.254 mm) sufficiently to recognize the location of wrinkles on knuckles of a human finger held directly behind the film.

Quantitatively, haze measurements according to a Haze Determination Test (defined below) can be less than about 75 percent, desirably less than about 70 percent, and preferably less than about 50 percent. Examples below demonstrate the possibility of achieving a haze of less than about 40 or even 30 percent.

It has been found that micrometer-sized particles of barium sulfate in a thermoplastic polyurethane cause haze of more than 90%. Conversely, it has been found that nano-sized particles of barium sulfate without optional dispersion aid result in haze of less than 75% in the compound. The difference between 75% and 90% is quite significant beyond the apparent simple arithmetic. When one confronts a compound with a haze of more than about 90%, the compound is so hazy as to appear nearly opaque. Optical translucency as defined above only begins to be possible when haze according to the Haze Determination Test drops below about 75%. As compounds are measured and found to have even lower haze value, as low as below 25%, the optical translucency definitely increases, but it important to note that the significant tipping point of optical translucency begins at about 75%. The introduction of the optional dispersion aid into the compound has been found to make it possible to drop well beneath 70% haze, but acceptable products can be made with haze between 70% and 75%.

The haze values identified above can be achieved with nano-sized particles of barium sulfate, even with the primary particles in aggregated or agglomerated morphology within the thermoplastic polyurethane. While total dispersion of totally deaggregated or deagglomerated primary particles is ideal to reach transparency of no measurable haze, the invention is based on use of the nano-sized particles of barium sulfate even though there may be aggregated and agglomerates remaining after dispersion of the particles into the thermoplastic polyurethane. Several means could be used to improve the dispersion, such as using dispersing agents or using various milling methods like an air jet mill.

Non-limiting embodiments are described below.

EMBODIMENTS OF THE INVENTION

TPU Resin

Thermoplastic polyurethane (TPU) is a desirable thermoplastic elastomer as it exhibits high tensile and tear strength, high flexibility at low temperatures, and extremely good abrasion and scratch resistance. TPU is also relatively stable against oil, fats and many solvents. Because of these desirable features, TPU can be beneficially used for a number of end-use applications, such as those in the health care industry. For simplicity, the term "polyurethane" as used herein includes polymers containing urethane (also known as carbamate) linkages, urea linkages, amide, or combinations thereof (i.e., in the case of poly(urethane-urea)s). Thus, thermoplastic polyurethanes of the invention contain at least urethane linkages and, optionally, urea or amide linkages.

A wide variety of TPU chemistries are suitable for use as the base TPU in the invention. For example, a number of aliphatic and aromatic chemistries can be used. One or more TPU chemistries can be used to form the TPU for compounds contained in this invention.

The term "aromatic" refers to TPUs derived from mononuclear aromatic hydrocarbon groups or polynuclear aromatic hydrocarbon groups. The term includes those TPUs derived from arylene groups. The term "arylene group" means a divalent aromatic group.

The term "aliphatic" refers to TPUs derived from saturated or unsaturated, linear, branched, or cyclic hydrocarbon groups. This term is used to encompass those TPUs derived from alkylene (e.g., oxyalkylene), aralkylene, and cycloalkylene (e.g., oxycycloalkylene) groups, for example. The term "alkylene group" means a saturated, linear or branched, divalent hydrocarbon group. Particularly preferred alkylene groups are oxyalkylene groups. The term "oxyalkylene group" means a saturated, linear or branched, divalent hydrocarbon group with a terminal oxygen atom. The term "aralkylene group" means a saturated, linear or branched, divalent hydrocarbon group containing at least one aromatic group. The term "cycloalkylene group" means a saturated, linear or branched, divalent hydrocarbon group containing at least one cyclic group. The term "oxycycloalkylene group" means a saturated, linear or branched, divalent hydrocarbon group containing at least one cyclic group and a terminal oxygen atom.

The neat thermoplastic urethane needs to be optically translucent, as defined above, in order to remain optically translucent in the compounds of the invention after dispersion of the radiopaque material and optionally, dispersion aid. Moreover, if used for a medical device, medical grade TPU approved by health agencies of governments, needs to be used.

A number of optically translucent, medical grade TPUs are sold, particularly under the Pellethane brand by Lubrizol Corporation. Of the various acceptable grades, Pellethane 2363-80AE polyurethane is presently preferred. As published by Lubrizol Corporation, PELLETHANE™ 2363-80AE elastomer is a polytetramethylene glycol based polyurethane elastomer used in healthcare applications. Its outstanding properties include superior resilience, low temperature properties, resistance to microorganisms, low extractables, excellent hydrolytic stability, and exceptionally smooth surfaces. It allows sterilization by dry heat, ethylene oxide or gamma radiation. Its typical applications include catheter components, tensioning ligatures, tubing, connectors and fittings. It satisfies medical grade requirements based on its USP Class VI test data for biocompatibility. Other medical TPU grades could also be applied of the present invention.

Radiopaque Material

As identified in PCT Publication WO95/14501, barium sulfate is commonly used as a radiopaque material. But in this invention, nano-sized particles of barium sulfate, as defined above, are used. These nano-sized particles of barium sulfate maximize the opportunity for the radiopaque material to minimize disruption of optical translucency of the neat TPU.

At this time, two known candidates for use as the radiopaque materials are Sachtosperse™ HU-D Amine Surface Treated Nano-BaSO$_4$ and Sachtosperse™ HU-N Nano-BaSO$_4$ without any surface treatment from Sachtleben Chemie GmbH of Duisburg, Germany. As advertised by Sachtleben, these two types of nano-sized particles of BaSO$_4$ are synthetic barium sulfate powders having an average particle sizes of less than 0.1 μm. Sachtosperse™ HU-D is treated with a triethanolamine (CAS #102-71-6) organic coating to enhance dispersibility with features such as a low refractive index, chemical inertness, high transparency, a pH of about 9, and a specific surface area of about 30 m$^2$/gram.

Optional Dispersion Aid

To achieve even better haze values according to the Haze Determination Test defined below of less than 70%, polyols, such as propylene glycol can be used to assist in the dispersion of the nano-sized particles of barium sulfate into the TPU. It has been found that a minor amount of propylene glycol is particularly suitable for use in dispersing nano-sized particles of barium sulfate into the TPU to retain sufficient optical translucency as define above. Other polyols, particularly diols and triols, have also been tried and found effective for dispersing the nano-sized particles of BaSO$_4$ into TPU. Non-limiting examples of other polyols include glycerol, polyethylene glycol.

As shown in the Examples below, an unexpected variety of other chemicals have been found to act as dispersion aids for the radiopaque material, including without limitation, sulfolane, triethyl citrate, and 1-methyl-2-pyrrolidinone. Though not as effective as polyols, these non-polyols result in haze values of less than 70%.

Also as shown in the Examples below, the dispersion aid may not be needed if the amount of radiopaque material is far less than 20 weight percent of the compound. But if 20 weight percent or more of radiopaque material is required for sufficient radiopacity, then one of the dispersion aids identified above is useful to meet the requirements of a haze of less than 70% using the Haze Determination Test.

Optional Surface Enhancer

Another desirable factor of making an in-vivo medical device, such as a catheter, is to have good surface smoothness to minimize abrasion of body tissues or accumulation of body fluids. When using nano-sized particles of barium sulfate in the polyurethane, it has been found that haze is reduced significantly, allowing the user to see through the catheter. But, those catheter tubes were also found to be somewhat rough on their external surfaces. Surface smoothness can minimize any body fluid accumulation, such as blood or its constituents, on any surface contacting such body fluids. Also surface smoothness can reduce abrasion of the medical device against body tissues.

A surface enhancer has been found to be desirable to include, optionally, into the compound of the invention. It has been found that minor amounts of fatty acids or fatty acid esters can enhance surface smoothness. For example, stearic acid and glycerol monostearate (GMS) were used in minor amounts and found to reduce roughness to achieve approximately the same amount of smoothness as now exists in catheters which use micro-sized particles of barium sulfate.

Thus, a trio of properties: radiopacity, optical translucency, and surface smoothness can be achieved.

Optional Additives

The compound of the present invention can include conventional plastic additives in an amount that is sufficient to obtain a desired processing or performance property for the compound. The amount should not be wasteful of the additive or detrimental to the processing or performance of the compound. Those skilled in the art of thermoplastics compounding, without undue experimentation but with reference to such treatises as Plastics Additives Database (2004) from Plastics Design Library (www.elsevier.com), can select from many different types of additives for inclusion into the compounds of the present invention.

Non-limiting examples of optional additives include adhesion promoters; biocides (antibacterials, fungicides, and mildewcides), anti-fogging agents; anti-static agents; bonding, blowing and foaming agents; dispersants; fillers and extenders; fire and flame retardants and smoke suppressants; impact modifiers; initiators; lubricants; micas; pigments, colorants and dyes; oils and plasticizers; processing aids; release agents; silanes, titanates and zirconates; slip and anti-blocking agents; stabilizers; stearates; ultraviolet light absorbers; viscosity regulators; waxes; and combinations of them. Anti-oxidants are particularly useful for these plastic compounds to provide additional durability.

Table 1 shows acceptable, desirable, and preferable ranges of ingredients useful in the present invention, all expressed in weight percent (wt. %) of the entire compound. The compound can comprise, consist essentially of, or consist of these ingredients.

TABLE 1

|  | Acceptable | Desirable | Preferable |
| --- | --- | --- | --- |
| TPU Resin | 44-89 | 61-84 | 70-79 |
| Nano-Sized Particles of Barium Sulfate | 11-50 | 15-25 | 19-21 |
| Optional Dispersion Aid | 0-6 | 1-5 | 1-4 |
| Optional Surface Enhancer | 0-5 | 0-4 | 1-3 |
| Optional Additives | 0-10 | 0-5 | 0-2 |

The amount of radiopacity required can vary according to ultimate usage. The selection of weight percent of nano-sized particles of barium sulfate can be made by persons having ordinary skill in the art depending on the depth of field for which the radiopacity is needed. Medical devices to be inserted deep into the human body for diagnosis or therapeutic purposes can include a greater weight percent of barium sulfate than a medical device to be inserted shallowly into the human body.

The weight percent ranges identified in Table 1 reflect the fully formed compound, not requiring any additional dilution with additional TPU resin. Nonetheless, it is possible to compute a masterbatch or concentrated form of the compound in the weight percent ranges identified in Table 1 based on the expected dilution or "let-down ratio." For example, a 3:1 let-down ratio of a masterbatch containing 40 weight percent of barium sulfate into TPU resin will result in 10 weight percent of the barium sulfate in the final TPU compound. Thus, it is possible to form the plastic articles from either a masterbatch/let-down approach or a fully compounded approach.

Processing

The preparation of compounds of the present invention has been found to offer some unexpected advantages and preferences, after the proper ingredients have been selected. The compound of the present invention can be made in batch or continuous operations.

Mixing in a continuous process typically occurs in an extruder that is elevated to a temperature that is sufficient to melt the polymer matrix with addition of all additives at the feed-throat, or by injection or side-feeders downstream. Extruder speeds can range from about 200 to about 700 revolutions per minute (rpm), and preferably from about 200 rpm. Typically, the output from the extruder is pelletized for later extrusion or molding into polymeric articles.

It has also been found that preparation of the masterbatch described above, before melt-mixing, can be preferable. In other words, some of the thermoplastic polyurethane, and all of the nano-sized particles of barium sulfate and all of the optional dispersion aid, if used, are formed into a masterbatch for feeding at the throat of the extruder with additional thermoplastic polyurethane for melt-mixing together.

Moreover, it has also been found that the preparation of the masterbatch benefits from both throat feeding and side feeding. In other words, the masterbatch is formed by feeding some of the thermoplastic polyurethane, the nano-sized particles of barium sulfate, and the dispersion aid, if used, into the throat of the extruder and feeding additional thermoplastic polyurethane at a downstream location for melt-mixing together.

Subsequent extrusion, molding, or film pressing techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (www.elsevier.com), one can make articles of any conceivable shape and appearance using compounds of the present invention.

USEFULNESS OF THE INVENTION

Any plastic article needing flexibility, elongation, and the physical properties of a TPU, and also radiopacity and optical translucency can benefit from TPU compounds of the present invention. The plastic article can be formed from the compound by molding, extruding, calendering, thermoforming, or 3D printing. As stated previously, medical devices benefit most from the physical properties of a TPU and optical translucency and radiopacity, particularly those which are used in-vivo and need radiopacity imaging during therapeutic or diagnostic procedures. Before use in-vivo, the optical translucency is beneficial for monitoring the condition within the medical device.

Non-limiting examples of plastic medical devices include tubing, connectors, catheters, heart valves, expandable trocars, etc.

Each of these medical devices can benefit from having surface smoothness for contact in-vivo with body fluids or tissues.

Examples further explain the invention.

EXAMPLES

Comparative Examples A-I and Examples 1-10

Table 2 shows the extrusion conditions. Tables 3 and 4 show the ingredients, recipes and the test results. Micro sized barium sulfate is the conventional material used for radiopaque applications. Its primary particle size (defined as the smallest particles observed by high resolution SEM in the sample) is about 0.5 micrometer to 1 micrometer. Nano-sized particles of barium sulfate is a different scale when fully dispersed and deagglomerated and deaggregated to be smaller than the wavelengths of visible light.

A method is defined here to judge the translucency of a TPU compound with nano-sized or micro-sized particles of barium sulfate. For purposes of this invention, this method shall be called "Haze Determination Test."

Samples of each of the Examples and Comparative Examples were prepared as follows. Polymer pellets were dried in oven at 90° C. for four hours. The dried materials were placed between clear polyester sheets, each of 2 mil (0.05 mm) thickness, and then placed on a heated press and the platens closed (380° F., 20,000 psi pressure (193° C., 138 MPa)) for 45 seconds. It was then cooled to produce a polymer test sample thickness of 5-10 mils (0.127-0.254 mm) (excluding the polyester sheets). The haze was measured using ASTM D1003 with the polyester sheets remaining in place for Comparative Examples A-I and Examples 1-10. Each polyester sheet is nearly transparent itself with a haze as low as 1% for the 2 mil (0.05 mm) thickness. The haze of the 7 mil (0.18 mm) sheet, between the two polyester sheets which have nearly no haze themselves, is reported as the percentage haze of compounds under testing.

In the event that one needs to determine haze of a strand or a catheter sample, a piece of the strand or catheter tube could be dried and then pressed also into a 7 mil (0.18 mm) sheet. Haze could be measured by ASTM D1003 to represent the quantitative translucency of the strand or the catheter sample.

All the Examples and Comparative Examples for the Haze Determination Test were evaluated using a BYK Gardner Haze-gard Plus Model 4725 haze meter. The instrument was properly calibrated based on the given procedure by the manufacturer before its use. Lower haze indicates better optical translucency, and haze results according to this Haze Determination Test are reported in the following Tables 3 and 4.

TABLE 2

| Extruder Conditions All Comparative Examples and Examples | |
|---|---|
| Extruder Type: Krupp Warner-Pfleiderer | 25 mm (L/D 44/1) Twin screw extruder |
| Zone 1 | 188° C. |
| Zone 2 | 193° C. |
| Zone 3 | 190° C. |
| Zone 4 | 188° C. |
| Zone 5 | 182° C. |
| Zone 6 | 182° C. |
| Zone 7 | 177° C. |
| Zone 8 | 171° C. |
| Die | 182° C. |
| RPM | 200 |
| Form of Product | Pellets |

TABLE 3

| | Examples | | | |
|---|---|---|---|---|
| Ingredients: | A | 1 | 2 | 3 |
| Pellethane 2363-80AE | 80.0 | 80.0 | 80.0 | 90.0 |
| Barium Sulfate, Micro- BaSO₄: Davos | 20.0 | | | |
| Sachtoperse HU-N, Nano- BaSO₄ | | 20.0 | | |
| Sachtoperse HU-D, Nano- BaSO₄ | | | 20.0 | 10.0 |
| Haze number (%) of 7 mil (0.18 mm) film using the Haze Determination Test | 90 | 74 | 73 | 40 |

TABLE 4

| | Examples | | | | | | | | | | | | | | |
|---|---|---|---|---|---|---|---|---|---|---|---|---|---|---|---|
| | B | C | D | E | F | G | H | I | 4 | 5 | 6 | 7 | 8 | 9 | 10 |
| Aerosil 200 silica | 0.6 | | | | | | | | | | | | | | |
| Polyacrylic acid | | 2.4 | | | | | | | | | | | | | |
| Polyvinylpyrrolidone | | | 2.4 | | | | | | | | | | | | |
| Cyclic PBT | | | | 5 | | | | | | | | | | | |
| Diethyl Succinate | | | | | 2.9 | | | | | | | | | | |
| Cabosil TS 720 silica | | | | | | 0.6 | | | | | | | | | |
| Zinc Stearate | | | | | | | 1 | | | | | | | | |
| Succinic Acid | | | | | | | | 3.3 | | | | | | | |
| Sulfolane | | | | | | | | | 3.3 | | | | | | |

TABLE 4-continued

| | Examples | | | | | | | | | | | | | | |
|---|---|---|---|---|---|---|---|---|---|---|---|---|---|---|---|
| | B | C | D | E | F | G | H | I | 4 | 5 | 6 | 7 | 8 | 9 | 10 |
| Triethyl citrate | | | | | | | | | | 3.9 | | | | | |
| 1-Methyl, 2 pyrrolidinone | | | | | | | | | | | 3.3 | | | | |
| Glycerol | | | | | | | | | | | | 2.9 | | | |
| Polyethylene glycol | | | | | | | | | | | | | 2.5 | | |
| Propylene Glycol 1, 3 | | | | | | | | | | | | | | 2.9 | |
| Propylene Glycol 1, 2 | | | | | | | | | | | | | | | 2.9 |
| Sachtoperse HU-D, Nano-BaSO$_4$ | 20 | 20 | 20 | 20 | 20 | 20 | 20 | 20 | 20 | 20 | 20 | 20 | 20 | 20 | 20 |
| Pellethane 2363-80AE | 79.4 | 77.6 | 77.6 | 75 | 77.1 | 79.4 | 79 | 76.7 | 76.7 | 76.1 | 76.7 | 77.1 | 77.5 | 77.1 | 77.1 |
| Haze number (%) of 7 mil (0.18 mm) film using the Haze Determination Test | 78 | 78 | 77 | 75 | 75 | 74 | 74 | 72 | 68 | 65 | 63 | 58 | 58 | 27 | 25 |

Reviewing Table 3, a comparison of Comparative Example A with Examples 1-3 shows that the particular size of particles of barium sulfate made a big difference of the optical translucency of the final composition. The conventional micro-scale barium sulfate (Comparative Example A) has a haze of 90%, while two samples using nano-sized particles of barium sulfate provided sufficient optical translucency (Examples 1 and 2), less than 75%. No difference between untreated (Example 1) and surface treated (Example 2) barium sulfate was observed. The lower the loading level of barium sulfate, the lower and better the haze number is, as demonstrated by comparing Examples 2 and 3. But also the extent of radiopacity is reduced.

Reviewing Table 4, in which various dispersion aids were used to further reduce haze of nano-sized particles of barium sulfate in polyurethane, one can conclude that both 1,2-propylene glycol (Example 10) and 1,3-propylene glycol (Example 9) are the most effective ones. Both unexpectedly reduced haze from 73% to below 30% with only 2.9 wt. % loading. These results are very surprising. Other polyols, polyethylene glycol (Example 8) and glycerol (Example 7) were also effective to reduce haze of nano-sized particles of barium sulfate in polyurethane composites below the 70% haze level.

Outside of the polyols, sulfolane (Example 4), trimethyl citrate (Example 5) and 1-methyl-2-pyrrolidinone (Example 6) also reduced haze of the nano-sized particles of barium sulfate in polyurethane composition. The other dispersion aids, (Examples B-I) do not show any positive effect on haze reduction of the nano-sized particles of barium sulfate compared with Examples 1 and 2 with no dispersion aids at all, suggesting only a selective group of dispersion aids work effectively if such aids are to be used.

Examples 11-13

Table 5 shows the formulations and Haze results for Examples 11-13, which employ a preferred embodiment of the use of a fatty acid or a fatty acid ester in the formulation to improve surface smoothness. Table 6 shows a qualitative comparison of surface smoothness of strand having a diameter of 2.5-3.5 mm for each Example 11-13 and Comparative Examples A-I and Examples 1-10. Qualitative testing of the surface smoothness of a strand is a good predictor of surface smoothness of the medical device, such as the tubular surface of a catheter. Examples 11-13 were extruded according to the processing conditions of Table 2.

TABLE 5

| Ingredients (Wt. %) | Ex. 11 | Ex. 12 | Ex. 13 |
|---|---|---|---|
| Glycerol monostearate | | 2 | 2 |
| Stearic acid | 2 | | |
| Propylene Glycol 1,2 | 1.5 | 1.5 | 1.5 |
| Sachtoperse HU-N, Nano-BaSO$_4$ | 20 | 20 | 20 |
| Pellethane 2363-75D | | | 76.5 |
| Pellethane 2363-80AE | 76.5 | 76.5 | |
| Haze (%) of 7 mil (0.18 mm) film using the Haze Determination Test | 55 | 58 | 28 |

TABLE 6

| | Strand Surface Smoothness (2.5-3.5 mm diameter) |
|---|---|
| Comparative Example A | +++ |
| Example 1-10 | + |
| Comparative Example B-I | + |
| Examples 11-13 | +++ |

Continuing with the better formulation of Example 10, each of Examples 11-13 used a smaller amount of Propylene Glycol 1,2 and the same amount of Nano-BaSO$_4$. Example 11 differed from Example 12 based on the difference between stearic acid and glycerol mono stearate, whereas Example 12 differed from Example 13 in respect of the grade of thermoplastic polyurethane used. In all three Examples, Haze was less than 60% and Example 13 was superior to the other two by a wide margin.

Considering Table 6, a qualitative test was performed using hand touch to the surface along the strand. The smoothness was much greater for Examples 11-13 as compared with both Examples 1-10 and Comparative Examples B-I. Indeed, Example 13 using Nano-BaSO$_4$ had the same level of smoothness as Comparative A which used Micro-BaSO$_4$.

Therefore, this embodiment of the invention using a surface enhancer achieved radiopacity, optical translucency, and surface smoothness.

The invention is not limited to the above embodiments. The claims follow.

What is claimed is:

1. A radiopaque, optically translucent thermoplastic compound, comprising:
   (a) thermoplastic polyurethane;
   (b) nano-sized particles of barium sulfate dispersed in the thermoplastic polyurethane at about 19 weight percent to 50 about 21 weight percent of the compound, wherein the nano-sized particles of barium sulfate have more than 50% of primary particles of the barium sulfate in a size in a largest dimension of less than or equal to 100 nanometers;

(c) dispersion aid at about 1 weight percent to about 4 weight percent of the compound, wherein the dispersion aid is selected from the group consisting of 1,2-propylene glycol, 1,3-propylene glycol, sulfolane, triethyl citrate, 1-methyl-2-pyrrolidinone, and combinations thereof; and (d) surface enhancer at about 1 weight percent to about 3 weight percent of the compound, wherein the surface enhancer is selected from the group consisting of fatty acids, fatty acid esters, and combinations thereof;

wherein a compressed film of the compound in a thickness of 0.18 mm has a haze of less than 70%, as measured using a Haze Determination Test.

2. The compound of claim 1, wherein the compressed film has a haze of less than 30%, as measured using the Haze Determination Test.

3. The compound of claim 1, wherein the dispersion aid is 1,2-propylene glycol or 1,3-propylene glycol or combinations thereof, and wherein the compressed film has a haze of less than 30%, as measured using the Haze Determination Test.

4. The compound of claim 1, wherein the fatty acid is stearic acid and wherein the fatty acid ester is glycerol monostearate.

5. A medical device made from the compound of claim 1.

6. The medical device of claim 5, in the form of a catheter.

7. The medical device of claim 5 in the form of tubing.

8. A radiopaque, optically translucent thermoplastic compound, comprising:

(a) thermoplastic polyurethane;

(b) nano-sized particles of barium sulfate dispersed in the thermoplastic polyurethane at about 15 weight percent to about 25 weight percent of the compound, wherein the nano-sized particles of barium sulfate have more than 50% of primary particles of the barium sulfate in a size in a largest dimension of less than or equal to 100 nanometers; and (c) dispersion aid at about 1 weight percent to about 4 weight percent of the compound, wherein the dispersion aid is selected from the group consisting of 1,2-propylene glycol, 1,3-propylene glycol, and combinations thereof;

wherein a compressed film of the compound in a thickness of 0.18 mm has a haze of less than 30%, as measured using a Haze Determination Test.

9. The compound of claim 8, wherein the dispersion aid is 1,2-propylene glycol, wherein the compound further comprises surface enhancer at about 1 weight percent to about 3 weight percent of the compound, and wherein the surface enhancer is glycerol monostearate.

10. A medical device made from the compound of claim 9.

11. The medical device of claim 10, wherein the medical device is in the form of a catheter or tubing.

* * * * *

UNITED STATES PATENT AND TRADEMARK OFFICE
CERTIFICATE OF CORRECTION

PATENT NO. : 9,913,934 B2  
APPLICATION NO. : 14/916687  
DATED : March 13, 2018  
INVENTOR(S) : Frautschi et al.

Page 1 of 1

It is certified that error appears in the above-identified patent and that said Letters Patent is hereby corrected as shown below:

In the Claims

Column 11, Line 1, Claim 1, "to 50 about 21 weight" should be changed to -- to about 21 weight --

Signed and Sealed this  
Twenty-sixth Day of March, 2019

Andrei Iancu  
*Director of the United States Patent and Trademark Office*